US009434673B2

(12) United States Patent
Gruene et al.

(10) Patent No.: US 9,434,673 B2
(45) Date of Patent: Sep. 6, 2016

(54) PROCESS FOR PREPARING VINYLIDENECARBOXYLIC ACID (ESTER)S BY REACTION OF FORMALDEHYDE WITH ALKYLCARBOXYLIC ACID (ESTER)S

(71) Applicant: BASF SE, Ludwigshafen (DE)

(72) Inventors: Philipp Gruene, Mannheim (DE); Cornelia Katharina Dobner, Ludwigshafen (DE); Marco Hartmann, Woerth (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/277,384

(22) Filed: May 14, 2014

(65) Prior Publication Data

US 2014/0343318 A1 Nov. 20, 2014

Related U.S. Application Data

(60) Provisional application No. 61/822,948, filed on May 14, 2013.

(30) Foreign Application Priority Data

May 14, 2013 (DE) ........................ 10 2013 008 206

(51) Int. Cl.
*B01J 27/198* (2006.01)
*C07C 51/347* (2006.01)
*C07C 67/347* (2006.01)
*C07C 51/353* (2006.01)

(52) U.S. Cl.
CPC ........... *C07C 51/347* (2013.01); *C07C 51/353* (2013.01)

(58) Field of Classification Search
CPC ... B01J 27/198; C07C 51/347; C07C 67/347
USPC .......................... 502/209; 562/599; 560/212
See application file for complete search history.

(56) References Cited

U.S. PATENT DOCUMENTS

| | | | |
|---|---|---|---|
| 3,864,280 A * | 2/1975 | Schneider ..................... | 502/209 |
| 4,132,670 A * | 1/1979 | Katsumoto et al. .......... | 502/209 |
| 4,165,438 A | 8/1979 | Schneider | |
| 4,795,818 A | 1/1989 | Becker et al. | |
| 5,137,860 A | 8/1992 | Ebner et al. | |
| 5,158,923 A | 10/1992 | Barone | |
| 5,296,436 A | 3/1994 | Bortinger | |
| 5,677,261 A | 10/1997 | Tenten et al. | |
| 8,686,194 B2 | 4/2014 | Macht et al. | |
| 8,785,344 B2 | 7/2014 | Karpov et al. | |
| 2008/0227992 A1 | 9/2008 | Dobner et al. | |
| 2013/0109871 A1 | 5/2013 | Rosendahl et al. | |
| 2013/0123517 A1 | 5/2013 | Karpov et al. | |
| 2014/0163290 A1 | 6/2014 | Grüne et al. | |
| 2014/0200380 A1 | 7/2014 | Josch et al. | |
| 2014/0221683 A1 | 8/2014 | Welker-Nieuwoudt et al. | |

FOREIGN PATENT DOCUMENTS

| | | |
|---|---|---|
| DE | 103 36 386 A1 | 3/2004 |
| DE | 10 2010 028 328 A1 | 11/2011 |
| DE | 10 2010 023 312 A1 | 12/2011 |
| EP | 0 124 380 A1 | 11/1984 |
| EP | 0 714 700 A2 | 6/1996 |
| WO | WO 95/26817 A1 | 10/1995 |
| WO | WO 97/12674 A1 | 4/1997 |
| WO | WO 2006/094766 A1 | 9/2006 |
| WO | WO 2007/012620 A1 | 2/2007 |

OTHER PUBLICATIONS

Mamoru Ai, Journal of Catalysis, (1987), vol. 107, p. 201-208 (cited in IDS).*
Christensen et al. Angew. Chem. Int. Ed., (2006), V45, p. 4648-4651.*
International Search Report and Written Opinion issued Aug. 5, 2014 in PCT/EP2014/059520 with English Translation of Category of Cited Documents.
M. Al, "Preparation of High- Surface-Area Titanium-Vanadium Binary Pyrophosphate Catalysts", Appli ed Catalysis, vol. 48, No. 1, Elsevier Science Publishers B.V., XP055034436, (Mar. 1, 1989), pp. 51-61.
Mamoru Al, Vapor-Phase Aldol Condensation of Formaldehyde with Acetic Acid on $V_2O_5$-$P_2O_5$ Catalysts, Journal of Catalysis, vol. 107, XP002667283, (Jan. 1, 1987), pp. 201-208.
Mamoru Al, "Partial Oxidation of Propylene on $V_2O_3$-$P_2O_5$—Based Catalysts", Journal of Catalysis, vol. 101, (1986), pp. 473-483.

* cited by examiner

*Primary Examiner* — Yong Chu
(74) *Attorney, Agent, or Firm* — Oblon, McClelland, Maier & Neustadt, L.L.P

(57) ABSTRACT

Process for preparing a vinylidenecarboxylic acid or ester thereof, wherein a reaction gas comprising gaseous formaldehyde, molecular oxygen and an alkycarboxylic acid or ester thereof is brought into contact with a solid catalyst whose active composition comprises a vanadium-phosphorus oxide having an average oxidation state of vanadium of from +4.40 to +5.0 to give a product gas comprising the vinylidenecarboxylic acid or ester thereof.

16 Claims, No Drawings

PROCESS FOR PREPARING VINYLIDENECARBOXYLIC ACID (ESTER)S BY REACTION OF FORMALDEHYDE WITH ALKYLCARBOXYLIC ACID (ESTER)S

The present invention relates to a process for preparing vinylidenecarboxylic acids and esters thereof by reaction of formaldehyde with alkylcarboxylic acids and esters thereof.

In particular, the present invention relates to a process for preparing acrylic acid by reaction of formaldehyde with acetic acid.

At present, the industrial preparation of acrylic acid is carried out essentially exclusively by heterogeneously catalyzed two-stage partial oxidation of propene (see, for example, DE-A 103 36 386).

An advantage of this mode of operation is that it has a comparatively high target product selectivity based on propene reacted. Recirculation of unreacted propene makes it possible to achieve high acrylic acid yields from the propene used.

At present, the industrial preparation of propene is carried out essentially from petroleum or propane-comprising natural gas. However, in view of the foreseeable scarcity of the fossil resources petroleum and natural gas, there will in future be a need for processes for preparing acrylic acid from alternative and/or renewable raw materials.

The preparation of vinylidenecarboxylic acids from alkylcarboxylic acids and formaldehyde, in particular the preparation of acrylic acid from acetic acid and formaldehyde, is prior art.

An advantage of this mode of operation is that formaldehyde is obtainable by partial oxidation of methanol. Methanol can in principle be produced via synthesis gas (gas mixtures of carbon monoxide and molecular hydrogen) from all carbon-comprising basic fossil materials and all carbon-comprising renewable raw materials.

U.S. Pat. No. 4,165,438 discloses a process for preparing acrylic acid and esters thereof, in which the reactants formaldehyde and a lower alkylcarboxylic acid or a lower alkyl ester thereof are reacted in the gas phase at from about 300° C. to 500° C. in the presence of a catalyst. The catalyst comprises mainly vanadium orthophosphate having an intrinsic surface area of from about 10 to about 50 m²/g and a P/V atomic ratio of from 1:1 to 1.5:1. The oxidation number of the vanadium is said to be from about 3.9 to 4.6. The catalyst is said to be activated by heating in an oxygen-comprising gas such as air, deactivated by use and reactivated by renewed heating. It is clear from column 5, lines 33 to 41, that the yield of acrylic acid greatly decreases after only 140 minutes in the process of the U.S. Pat. No. 4,165,438.

EP 0 124 380 A1 discloses a process for preparing unsaturated carboxylic acids and esters, in which a gaseous mixture of a saturated monocarboxylic acid or an ester thereof is reacted with formaldehyde or a formaldehyde derivative in the presence of oxygen over a catalyst in the form of a multimetal oxide in a reaction zone.

Journal of Catalysis, 107, 1987, 201-208, discloses processes for the aldol condensation of formaldehyde and acetic acid in the gas phase. Experiments in which the aldol condensation was carried out in the presence of 2.2% by volume of oxygen over a V₂O₅—P₂O₅ catalyst having a PN atomic ratio of 1.06 are described on page 203 in the right-hand column, line 5 onward. It can be seen from FIG. 4 that the molar yield of acrylic acid is independent of whether or not oxygen is present and is, at 25 mol % at temperatures of from 300 to 325° C., low. In addition, it can be seen from FIG. 4 that although the molar yield of acrylic acid increases with increasing temperature, the molar proportion of the undesirable by-product $CO_x$ is about equal to the molar proportion of the acrylic acid present. The production of the catalysts used was carried out as described in the U.S. Pat. No. 4,132,670 and in Journal of Catalysis, 101, 1986, 473-483. As shown in the examples below for reproducing the $V_2O_5$—$P_2O_5$ catalyst, the oxidation number of the vanadium in the catalyst is from 4.21 to 4.23.

It was an object of the present invention to provide a process for preparing vinylidenecarboxylic acids and esters thereof, which process does not have the disadvantages of the processes of the prior art. In particular, it was an object to provide a process which ensures a high conversion of the formaldehyde used and a high selectivity of the conversion of formaldehyde into vinylidenecarboxylic acid or an ester thereof over a long period of time.

The object is achieved by a process for preparing a compound of the formula (I),

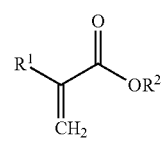

where $R^1$ and $R^2$ are each, independently of one another, H or $(C_1$-$C_4)$-alkyl, wherein a reaction gas comprising gaseous formaldehyde, molecular oxygen and a gaseous compound of the formula (II)

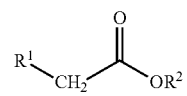

is brought into contact with a solid catalyst whose active composition comprises a vanadium-phosphorus oxide having an average oxidation state of vanadium of from +4.40 to +5.0, preferably from +4.48 to +5.0, more preferably from >+4.60 to +5.0, particularly preferably from >+4.65 to +4.99, particularly preferably from >+4.69 to +4.99,
to give a product gas comprising the compound of the formula (I).

The equilibrium present in the preparative process of the invention is shown in scheme 1.

(Scheme 1)

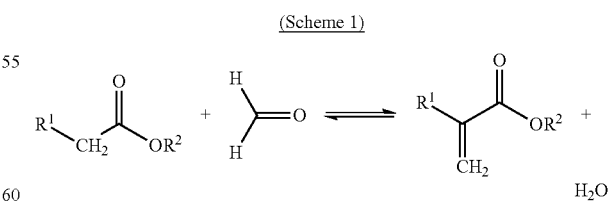

The process of the invention makes it possible to convert an alkylcarboxylic acid which is able to undergo a condensation reaction with formaldehyde into a vinylidenecarboxylic acid. The process of the invention makes it possible to convert an alkylcarboxylic ester which is able to undergo a condensation reaction with formaldehyde into a vinylidenecarboxylic ester. The reaction between formaldehyde and alkylcarboxylic acid or alkylcarboxylic ester liberates one equivalent of water (condensation reaction, see scheme 1).

Preference is given to using acetic acid, methyl acetate, propanoic acid or methyl propionate as compound of the formula (II). Preference is thus given to a process in which $R^1$ and $R^2$ in the compounds of the formulae (I) and (II) are H or $CH_3$. If acetic acid is used as compound of the formula (II), acrylic acid is obtained as compound of the formula (I). If methyl acetate is used as compound of the formula (II), methyl acrylate is obtained as compound of the formula (I). If propionic acid is used as compound of the formula (II), methacrylic acid is obtained as compound of the formula (I). If methyl propionate is used as compound of the formula (II), methyl methacrylate is obtained as compound of the formula (I).

Particular preference is given to using acetic acid as compound of the formula (II). Particular preference is thus given to a process in which the compound of the formula (I) is acrylic acid and the compound of the formula (II) is acetic acid.

In all the following embodiments of the process of the invention, $R^1$ and $R^2$ are preferably H or $CH_3$.

In all the following embodiments of the process of the invention, the compound of the formula (I) is particularly preferably acrylic acid and the compound of the formula (II) is particularly preferably acetic acid.

In a preferred embodiment of the process, the reaction gas further comprises an inert diluent gas, preferably an inert diluent gas other than water vapor. For the purposes of the present invention, an inert diluent gas is a gas which is inert under the conditions which prevail in the process of the invention. An inert reaction gas constituent remains chemically unchanged to an extent of more than 95 mol %, preferably more than 97 mol %, or more than 98 mol %, or more than 99 mol %, in the process of the invention. Examples of inert diluent gases are $N_2$, $CO_2$, $H_2O$ and noble gases such as Ar and also mixtures of the abovementioned gases. Molecular nitrogen is preferably used as inert diluent gas in the process of the invention.

Water vapor plays a special role as inert diluent gas since it is both obtained as by-product (scheme 1) and is also comprised in some of the formaldehyde sources mentioned below and also possibly as impurity in formaldehyde and/or the compound of the formula (II) and generally adversely affects the desired condensation reaction. The water vapor content in the reaction gas is preferably from 0 to 50% by volume, more preferably from 0 to 30% by volume, particularly preferably from 0 to 20% by volume. An increased water vapor content decreases the conversion under given reaction conditions. This effect can be at least partly compensated by increasing the reaction temperature.

The proportion of the inert diluent gas in the reaction gas is preferably from 50 to 95% by volume, more preferably from 60 to 90% by volume, particularly preferably from 70 to 90% by volume.

According to the invention, from 60 to 100% by volume, preferably from ≥80 to 100% by volume, particularly preferably from ≥90 to 100% by volume, of the inert diluent gas other than water vapor is molecular nitrogen.

The reaction gas can comprise at least one reaction gas constituent which is predominantly present in solid form as "solid reaction gas constituent" under standard conditions (20° C., 1013 mbar) (for example some of the formaldehyde sources described below, e.g. trioxane). The reaction gas can further comprise at least one reaction gas constituent which is predominantly present in liquid form as "liquid reaction gas constituent" under standard conditions (e.g. acetic acid). The reaction gas can additionally comprise a reaction gas constituent which is predominantly present in gaseous form as "gaseous reaction gas constituent" under standard conditions (e.g. formaldehyde).

The production of the reaction gas can comprise bringing nongaseous reaction gas constituents into the gas phase and combining all reaction gas constituents. The reaction gas constituents can be brought into the gas phase and combined in any order. At least one of the gaseous reaction gas constituents and/or a solid reaction gas constituent can also firstly be at least partly taken up in at least one liquid reaction gas constituent and subsequently brought together with the liquid reaction gas constituent into the gas phase.

The bringing into the gas phase is effected by vaporization, preferably by supplying heat and/or reducing the pressure. The nongaseous reaction gas constituents can be introduced into gaseous reaction gas constituents in order to aid the vaporization of the nongaseous reaction gas constituents. Preference is given to placing a solution which comprises at least one liquid reaction gas constituent and may optionally comprise other reaction gas constituents into a reservoir and conveying the solution in the reservoir at the desired volume flow, e.g. by means of a pump, into a gaseous stream of preheated reaction gas constituents. The combining of the solution in the reservoir with the gaseous stream of preheated reaction gas constituents can be carried out, for example, in a vaporizer coil.

In the production of the reaction gas, it should, in particular, be noted that formaldehyde can also be introduced in the form of at least one of the formaldehyde sources mentioned below. Depending on the choice of formaldehyde source, this can be present in liquid, solid and/or gaseous form under standard conditions. Depending on the choice of formaldehyde source, the formaldehyde can be liberated from the formaldehyde source before and/or after bringing into the gas phase. In the reaction gas, the formaldehyde can also have been only partly liberated from the formaldehyde source.

The reaction gas is generally brought into contact with the catalyst at a reaction temperature of from 250 to 400° C., preferably from 260 to 390° C., more preferably at from 270 to 380° C., particularly preferably from 290 to 370° C., more particularly preferably from 290 to 340° C. and very particularly preferably from 300 to 325° C. The reaction temperature is the temperature of the reaction gas present in the catalyst bed averaged over the volume of the catalyst. The reaction temperature is calculated from the temperature profile of the catalyst bed. In the case of an isothermal reaction, the reaction temperature is the same as the temperature which is set at the outer wall of the reactor. A heating device can be used to set the temperature. The reaction gas is preferably fed to the reaction zone with a temperature in the range from 160 to 400° C. The reaction gas can be brought into contact with a solid inert material before being brought into contact with the catalyst. In contact with the solid inert material, the temperature of the reaction gas can be set to the value with which the reaction gas is to come into contact with the catalyst.

The total pressure of the reaction gas, i.e. the pressure prevailing in the reaction gas over the catalyst, can be either greater than or equal to 1 bar or less than 1 bar. The total pressure of the reaction gas is preferably from 1.0 bar to 50 bar, more preferably from 1.0 to 20 bar, particularly preferably from 1.0 to 10 bar, very particularly preferably from 1.0 to 6.0 bar.

All pressures indicated in this text are absolute pressures.

The catalyst can be present in the form of a fluidized bed. The catalyst is preferably present in the form of a fixed bed.

The catalyst is preferably arranged in a reaction zone. The reaction zone can be arranged in a heat exchanger reactor which has at least one primary space and at least one secondary space. The primary space and the secondary space are separated from one another by a dividing wall. The primary space comprises the reaction zone in which at least the catalyst is arranged. A fluid heat transfer medium flows through the secondary space. Heat is exchanged through the dividing wall with the purpose of modifying and controlling the temperature of the reaction gas in contact with the catalyst (i.e. regulate the temperature of the reaction zone).

Furthermore, the reaction zone can be located in an adiabatic reactor. In an adiabatic reactor, the heat of reaction is not removed via a dividing wall by thermal contact with a heat transfer medium, for instance a fluid heat transfer medium, but instead remains predominantly in the reaction zone. As a result of the adiabatic conditions, the temperature of the reaction gas and product gas increases over the length of the reactor in the case of an exothermic reaction.

The vanadium-phosphorus oxide preferably has a phosphorus/vanadium atomic ratio of from 0.9 to 2.0, preferably from 0.9 to 1.5, particularly preferably from 0.9 to 1.3 and very particularly preferably from 1.0 to 1.2. Furthermore, the vanadium-phosphorus oxide preferably has a specific BET surface area of at least 10 m$^2$/g, preferably from 10 to 50 m$^2$/g and very particularly preferably from 10 to 40 m$^2$/g. All specific surface areas indicated in the present text relate to determinations in accordance with DIN 66131 (determinations of the specific surface area of solids by gas adsorption (N$_2$) according to the Brunauer-Emmet-Teller (BET) method).

The catalysts used in the process of the invention display particularly high selectivities for formation of the compound of the formula (I) combined with a high conversion of formaldehyde.

The active composition can be doped with various promoter elements other than vanadium and phosphorus. Possible promoter elements of this type are the elements other than P and V of groups 1 to 15 of the Periodic Table. Doped vanadium-phosphorus oxides are disclosed by, for example, WO 97/12674, WO 95/26817, U.S. Pat. No. 5,137,860, U.S. Pat. No. 5,296,436, U.S. Pat. No. 5,158,923, U.S. Pat. No. 4,795,818 and WO 2007/012620.

Promoters which are preferred according to the invention are the elements lithium, potassium, sodium, rudidium, cesium, thallium, molybdenum, zinc, hafnium, zirconium, titanium, chromium, manganese, nickel, copper, iron, boron, silicon, tin, niobium, cobalt and bismuth, among which, apart from iron, particular preference is given to niobium, molybdenum, zinc and bismuth. The active compositions can comprise one or more promoter elements. The total content of promoters in the active catalytic composition is, based on the weight of the composition, preferably not more than 5% by weight (as individual promoter element in each case calculated as electrically neutral oxide in which the promoter element has the same valence (oxidation number) as in the active composition).

The vanadium-phosphorus oxide particularly preferably corresponds to the general formula (III),

$$V_1P_bX^1_dX^2_eO_n \quad (III),$$

where
X$^1$ is Fe, Mo, Bi, Co, Ni, Si, Zn, Hf, Zr, Ti, Cr, Mn, Cu, B, Sn and/or Nb, preferably Fe, Nb, Mo, Zn and/or Hf, X$^2$ is Li, K, Na, Rb, Cs and/or Tl,
b is from 0.9 to 2.0, preferably from 0.9 to 1.5, particularly preferably from 0.9 to 1.3 and very particularly preferably from 1.0 to 1.2,
d is from ≥0 to 0.1,
e is from ≥0 to 0.1, and
n is the stoichiometric coefficient of the element oxygen which is determined by the stoichiometric coefficient of the elements other than oxygen and their valence in (III).

The catalyst can be present as all-active shaped catalyst bodies or coated catalysts. A pulverulent active composition can also be used as catalyst.

The all-active shaped catalyst bodies can consist essentially of active composition (undiluted all-active shaped catalyst bodies). The active composition can also be present in diluted form in the all-active shaped catalyst bodies (diluted all-active shaped catalyst bodies), where at least one essentially inert diluent material is then comprised in the all-active shaped catalyst bodies. The diluent material is preferably selected from among finely divided aluminum oxide, silicon dioxide, aluminosilicates, zirconium dioxide, titanium dioxide. Undiluted all-active shaped catalyst bodies are preferred according to the invention. The all-active shaped catalyst bodies can have any shape.

Preferred regularly shaped all-active shaped catalyst bodies are spheres, solid cylinders, hollow cylinders and trilobes whose longitudinal dimension is in all cases advantageously from 1 to 10 mm. Preferred irregularly shaped all-active shaped catalyst bodies are, for example, fragments of regularly shaped all-active shaped catalyst bodies.

The production of the all-active shaped catalyst bodies preferably starts out from catalyst precursor composition and comprises a shaping process and the thermal treatment described below. The shaping process preferably comprises tableting, ram extrusion and/or screw extrusion. The thermal treatment which is specified in more detail below can be carried out at least partly before the shaping process and/or at least partly after the shaping process. The catalyst precursor composition is preferably admixed at least with a shaping aid such as graphite or mineral fibers before shaping.

The external diameter of cylindrical all-active shaped catalyst bodies is, in accordance with the use, advantageously from 3 to 10 mm, preferably from 4 to 8 mm and especially from 5 to 7 mm. Their height is advantageously from 1 to 10 mm, preferably from 2 to 6 mm and especially from 3 to 5 mm. The same dimensions are also preferred in the case of hollow-cylindrical all-active shaped catalyst bodies, with the internal diameter of the opening running from the top through to the bottom advantageously being from 1 to 8 mm, preferably from 2 to 6 mm and very particularly preferably from 2 to 4 mm. A wall thickness of from 1 to 3 mm is advantageous for the use in the case of hollow cylinders.

Coated catalysts comprise active composition applied to the surface of inert shaped support bodies. In the production of the coated catalysts, the surface of an inert shaped support body is coated with a pulverulent active composition or with a pulverulent catalyst precursor composition which has not yet been or been only partially thermally treated in combination with a liquid binder. At least part of the thermal treatment is carried out after coating when the inert shaped support body is coated with catalyst precursor composition which has not yet been or been only partially thermally treated. Inert shaped support bodies normally differ from the active composition in that they have a significantly lower specific surface area. In general, their specific surface area is less than 3 m²/g of shaped support body.

Suitable materials for the inert shaped support bodies are, for example, quartz, fused silica, sintered silica, sintered or fused alumina, porcelain, sintered or fused silicates such as aluminum silicate, magnesium silicate, zinc silicate, zirconium silicate and in particular steatite (e.g. steatite C 220 from CeramTec). The geometry of the inert shaped support bodies can in principle be irregular, but regularly shaped support bodies such as spheres or hollow cylinders are preferred according to the invention. The longitudinal dimension of the abovementioned inert shaped support bodies is, in terms of the use, advantageously from 1 to 10 mm for the purposes of the invention.

Coating of the inert shaped support bodies with the pulverulent active composition or the pulverulent catalyst precursor composition which has not yet been or been only partially thermally treated is preferably carried out in a suitable rotatable vessel, e.g. in a coating drum. A liquid binder containing an adhesive liquid is, in terms of the use, advantageously sprayed onto the inert shaped support bodies and the surface which has been moistened with the binder of the shaped support bodies being agitated in the coating drum is dusted with the pulverulent composition (cf., for example, EP-A 714 700). Finally, the adhesive liquid is generally at least partly removed from the coated shaped support body (e.g. by passing hot gas through the coated shaped support bodies, as described in WO 2006/094766). However, all other application methods acknowledged in EP-A 714 700 as prior art can in principle also be employed for producing the relevant coated catalyst. Possible liquid binders are, for example, water and aqueous solutions (e.g. of glycerol in water). For example, coating of the shaped support bodies can also be carried out by spraying a suspension of the pulverulent composition to be applied in a liquid binder (e.g. water) onto the surface of the inert shaped support bodies (generally with supply of heat and a drying entrainer gas). Coating can in principle also be carried out in a fluidized-bed unit or powder coating plant.

The layer thickness of the active composition applied to the surface of the inert shaped support body is from 10 to 2000 μm, preferably from 10 to 500 μm, more preferably from 100 to 500 μm, particularly preferably from 200 to 300 μm. Suitable coated catalysts are, inter alia, those whose inert shaped support body has the shape of a hollow cylinder having a length in the range from 3 to 6 mm, an external diameter in the range from 4 to 8 mm and a wall thickness in the range from 1 to 2 mm. In addition, all ring geometries disclosed in DE-A 102010028328 and in DE-A 102010023312 and also all those disclosed in EP-A 714 700 for possible inert shaped support bodies of ring-shaped catalysts are suitable.

In a preferred embodiment of the process, an all-active shaped catalyst body consisting of active composition is obtained by reacting a pentavalent vanadium compound, preferably $V_2O_5$, with an organic, reducing solvent, preferably isobutanol, in the presence of a pentavalent phosphorus compound, preferably orthophosphoric and/or pyrophosphoric acid, to give a catalyst precursor composition, shaping the catalyst precursor composition to give all-active shaped catalyst precursor bodies and treating these in an atmosphere comprising molecular oxygen at a temperature which generally exceeds 250° C., preferably 300° C., particularly preferably 350° C., but normally does not exceed 700° C., preferably does not exceed 650° C. and very particularly preferably does not exceed 600° C.

The high average oxidation state of the vanadium according to the invention is achieved by the treatment in the atmosphere comprising molecular oxygen. The treatment is preferably carried out in a "thermal treatment" before introduction of the catalyst into the reactor. It can also be carried out at least partially in the reactor in the "activation".

For example, production of the catalyst can comprise the following steps:
a) reaction of a pentavalent vanadium compound (e.g. $V_2O_5$) with an organic, reducing solvent (e.g. an alcohol such as isobutanol) in the presence of a pentavalent phosphorus compound (e.g. orthophosphoric and/or pyrophosphoric acid) with heating to from 75 to 205° C., preferably from 100 to 120° C.;
b) cooling of the reaction mixture to advantageously from 40 to 90° C.;
c) isolation (e.g. by filtration) of the solid catalyst precursor composition comprising V, P, O which is formed;
d) drying and/or thermal pretreatment of the catalyst precursor composition (optionally until commencement of preactivation by elimination of water from the catalyst precursor composition);
e) addition of shaping aids such as finely divided graphite or mineral fibers and subsequent shaping to give all-active shaped catalyst precursor bodies by, for example, tableting;
f) subsequently at least one thermal treatment of the resulting all-active shaped catalyst precursor bodies by heating in an atmosphere comprising oxygen, nitrogen, noble gases, carbon dioxide, carbon monoxide and/or water vapor. In the thermal treatment, the temperature generally exceeds 250° C., preferably 300° C., particularly preferably 350° C., but normally does not exceed 700° C., preferably does not exceed 650° C. and very particularly preferably does not exceed 600° C.

Preference is given to a thermal treatment in which a catalyst precursor is
(i) heated in an oxidizing atmosphere having an oxygen content of from 2 to 21% by volume to a temperature of from 200 to 350° C. and maintained under these conditions for a period of from 0.5 to 10 hours; and
(ii) heated in a nonoxidizing atmosphere having an oxygen content of ≤0.5% by volume and a hydrogen oxide content of from 20 to 75% by volume to a temperature of from 300 to 500° C. and maintained under these conditions for ≥0.5 hour; and
(iii) heated in an oxidizing atmosphere having an oxygen content of from 2 to 21% by volume to a temperature of from 250 to 700° C., preferably from 300 to 650° C., particularly preferably from 350 to 600° C., and maintained under these conditions until the desired average oxidation state of vanadium has been obtained.

The catalyst precursor can be either an all-active shaped catalyst precursor body or a catalyst precursor composition.

In step (i), the catalyst precursor is kept in an oxidizing atmosphere having a content of molecular oxygen of generally from 2 to 21% by volume and preferably from 5 to 21% by volume at a temperature of from 200 to 350° C. and preferably from 250 to 350° C. for a period of from 0.5 to 4 hours, preferably from 1 to 2 hours. In general, mixtures of oxygen, inert gases (e.g. nitrogen or argon), hydrogen oxide (water vapor) and/or air and also air are used in step (i). The temperature can be kept constant or can on average increase or decrease during step (i). Step (i) is generally preceded by a heating-up phase. In this heating-up phase, the temperature will firstly increase and then oscillate to the desired final value.

In step (ii), the catalyst precursor is kept in nonoxidizing atmosphere having a content of molecular oxygen of ≤0.5% by volume and of hydrogen oxide (water vapor) of from 20 to 75% by volume, preferably from 30 to 60% by volume, at a temperature of from 300 to 500° C. and preferably from 350 to 450° C. for a period of ≥0.5 hour, preferably from 2 to 10 hours and particularly preferably from 2 to 4 hours. The nonoxidizing atmosphere comprises, apart from the hydrogen oxide mentioned, generally predominantly nitrogen and/or noble gases such as argon, but this does not constitute a restriction. Gases such as carbon dioxide are also suitable in principle. The nonoxidizing atmosphere preferably comprises ≥40% by volume of nitrogen. The temperature can be kept constant during step (ii), or on average increase or decrease. If step (ii) is carried out at a higher or lower temperature than step (i), a heating-up or cooling phase is generally inserted between steps (i) and (ii).

In step (iii), the catalyst precursor is heated in an oxidizing atmosphere having an oxygen content of from 2 to 21% by volume to a temperature of from 250 to 700° C., preferably from 300 to 650° C., particularly preferably from 350 to 600° C., and maintained under these conditions until the desired average oxidation state of vanadium has been obtained. The time for which the heat treatment in step (iii) is maintained is, in the process of the invention, preferably selected so that the average oxidation state of vanadium is brought to a value of from +4.40 to +5.0, preferably from +4.48 to +5.0, more preferably from >+4.60 to +5.0, particularly preferably from >+4.65 to +4.99, very particularly preferably from >+4.69 to +4.99.

Since determination of the average oxidation state of vanadium during the thermal treatment is extremely difficult in terms of apparatus and time, the time required is advantageously determined experimentally in preliminary tests. This is generally carried out by means of a trial in which heat treatment is carried out under defined conditions and the samples are removed from the system after various times, cooled and analyzed to determine the average oxidation state of vanadium.

The period of time required in step (iii) is generally dependent on the nature of the catalyst precursor, the temperature set and the gas atmosphere selected, in particular the oxygen content. In general, the period of time in step (iii) is from 6 hours to 2 weeks, preferably from 12 hours to 1 week, particularly preferably from 1 to 6 days.

Further steps are possible before, between and/or after steps (i), (ii) and (iii) in the thermal treatment. Without implying a limitation, mention may be made of, for example, changes in the temperature (heating-up, cooling), changes in the gas atmosphere (alteration of the gas atmosphere), further hold times, transfers of the catalyst precursor into other apparatuses (e.g. to produce all-active shaped catalyst precursor bodies from a catalyst precursor composition) or interruptions of the overall thermal treatment as further steps.

Since the catalyst precursor generally has a temperature of <100° C. before commencement of the thermal treatment, this usually has to be heated up before step (i). Heating can be carried out using various gas atmospheres. The heating is preferably carried out in an oxidizing atmosphere as defined under step (i).

Before the catalyst is brought into contact with the reaction gas, an activation can be carried out in the reactor. In the activation, an activating gas which comprises molecular oxygen and is essentially free of organic constituents is passed over the catalyst at a temperature of from 200 to 450° C. The activation can take from a few minutes to a number of days. In the activation, the pressure of the activating gas mixture and its residence time over the catalyst are preferably set to values similar to the pressure of the reaction gas and its residence time over the catalyst in the preparation of the compound of the formula (I). The activating gas mixture comprises molecular oxygen and at least one inert activating gas constituent selected from among $N_2$, CO, $CO_2$, $H_2O$ and noble gases such as Ar. In general, the activating gas comprises from 0.5 to 22% by volume, preferably from 1 to 20% by volume and in particular from 1.5 to 18% by volume, of molecular oxygen. Preference is given to using air as a constituent of the activating gas mixture.

The residence time of the reaction gas in contact with the catalyst is not subject to any restrictions. It is generally in the range 0.3-15.0 s, preferably 0.7-13.5 s, particularly preferably 1.0-12.5 s. The ratio of the flow of reaction gas to the volume of the catalyst is preferably 200-5000 $h^{-1}$, preferably 250-4000 $h^{-1}$ and more preferably 300-3500 $h^{-1}$.

The space velocity of formaldehyde over the catalyst (expressed in an $g_{formaldehyde}/(g_{catalysat}*hour)$) is generally 0.01-3.0 $h^{-1}$, preferably 0.015-1.0 $h^{-1}$, and more preferably 0.02-0.5 $h^{-1}$.

The content of compound of the formula (II) in the reaction gas is from 1.5 to 20% by volume, preferably from 2 to 18% by volume, particularly preferably from 3 to 15% by volume, in the process of the invention.

The content of oxygen in the reaction gas is from 0.1 to 10% by volume, preferably from 0.3 to 7.5% by volume, particularly preferably from 0.5 to 5.0% by volume, in the process of the invention. The deactivation of the catalyst is delayed in the presence of oxygen.

The content of formaldehyde and/or formaldehyde source in the reaction gas is from 0.5 to 10% by volume, preferably from 1 to 9.0% by volume, particularly preferably from 2.0 to 8.0% by volume, calculated as formaldehyde, in the process of the invention.

In a preferred embodiment, the process of the invention additionally comprises the provision of formaldehyde from a formaldehyde source selected from among trioxane, paraformaldehyde, formalin, methylal, aqueous paraformaldehyde solution or aqueous formaldehyde solution, or by heterogeneously catalyzed partial gas-phase oxidation of methanol.

Trioxane is a heterocyclic compound which is formed by trimerization of formaldehyde and decomposes into monomeric formaldehyde on heating. Since the reaction gas is brought into contact with the catalyst at elevated temperature (in general above 250° C.), trioxane is a well-suited formaldehyde source. Since trioxane dissolves in water and in alcohols, corresponding trioxane solutions can also be used as formaldehyde sources for the process of the invention. A content of sulfuric acid in trioxane solutions of from 0.25 to 0.50% by weight aids the dissociation to form formaldehyde. As an alternative, the trioxane can also be dissolved in a liquid consisting mainly of the compound of the formula (II) and the resulting solution can be vaporized in order to produce the reaction gas and the trioxane comprised therein can be dissociated into formaldehyde at the elevated temperature.

Aqueous formaldehyde solution having, for example, a formaldehyde content of from 35 to 50% by weight can be procured commercially as formalin. Formalin usually comprises small amounts of methanol as stabilizer. These can, based on the weight of the formalin, amount to from 0.5 to 20% by weight, preferably from 0.5 to 5% by weight and particularly preferably from 0.5 to 2% by weight. After having been brought into the vapor phase, the formalin can be used directly for providing the reaction gas.

In the process described here it is in principle possible to use, inter alia, all aqueous formaldehyde solutions having a concentration of 1-100% by weight. However, preference is given to concentrated formaldehyde solutions comprising 48-90% by weight, or particularly preferably 60-80% by weight, of formaldehyde in aqueous solution as starting material. Appropriate processes for concentrating such formaldehyde solutions are known prior art and are described, for example, in WO 04/078690, WO 04/078691 or WO 05/077877.

Paraformaldehyde is the short-chain polymer of formaldehyde whose degree of polymerization is typically from 8 to 100. It is a white powder which is dissociated into formaldehyde at low pH values or on heating.

When paraformaldehyde is heated in water, it decomposes to give an aqueous formaldehyde solution which is likewise suitable as formaldehyde source. It is sometimes referred to as aqueous "paraformaldehyde solution" to distinguish it terminologically from aqueous formaldehyde solutions produced by dilution of formalin. However, in actual fact paraformaldehyde as such is essentially insoluble in water.

Methylal (dimethoxymethane) is a reaction product of formaldehyde with methanol, which is present as a colorless fluid at atmospheric pressure and 25° C. In aqueous acids, it is hydrolyzed to form formaldehyde and methanol. After being brought into the vapor phase, both methylal and the hydrolysate formed in aqueous acid can be used directly for providing the reaction gas.

On an industrial scale, formaldehyde is prepared by heterogeneously catalyzed partial gas-phase oxidation of methanol. According to the invention, particular preference is given to providing the formaldehyde by heterogeneously catalyzed partial gas-phase oxidation of methanol. In this embodiment, the formaldehyde is introduced as product gas from a heterogeneously catalyzed partial gas-phase oxidation of methanol to form formaldehyde to the reaction gas, optionally after part or all of any unreacted methanol comprised in the product gas has been separated off.

Although the presence of oxygen in the reaction gas retards the deactivation of the catalyst, the activity of the catalyst can decrease over prolonged periods of time. To increase the activity of the catalyst again, a regeneration step can be carried out between in each case two production steps in which the compound of the formula (I) is prepared. In the regeneration step, a regeneration gas which comprises molecular oxygen and is essentially free of organic constituents is passed over the catalyst at a temperature of from 200 to 450° C. The regeneration step can take from a few minutes to a number of days. The pressure of the regeneration gas and its residence time over the catalyst in the regeneration step are preferably set to values similar to the pressure of the reaction gas and its residence time over the catalyst in the production step. The regeneration gas comprises molecular oxygen and at least one inert regeneration gas constituent selected from among $N_2$, $CO$, $CO_2$, $H_2O$ and noble gases such as Ar. In general, the oxygen-comprising regeneration gas comprises from 0.5 to 22% by volume, preferably from 1 to 20% by volume and in particular from 1.5 to 18% by volume, of molecular oxygen. Preference is given to using air as a constituent of the regeneration gas.

In a preferred embodiment of the process, the compound of the formula (I) is isolated by fractional condensation of the product gas. Here, the temperature of the product gas is reduced, optionally firstly by direct and/or indirect cooling, and is subsequently introduced into a condensation zone in which the product gas condensed spontaneously in an ascending fashion to give fractions. The condensation zone is preferably located within a condensation column which is equipped with separation-active internals (e.g. mass transfer plates) and is optionally provided with cooling circuits. Appropriate selection of a number of theoretical plates gives the compound of the formula (I) in the form of a first fraction which consists predominantly, preferably to an extent of at least 90% by weight, particularly preferably at least 95% by weight, of the compound of the formula (I). Particular preference is given to configuring the fractional condensation, in particular in respect of a number of theoretical plates, so that, in addition to the compound of the formula (I) in the form of the first fraction, the unreacted compound of the formula (II) is obtained in the form of a second fraction which consists predominantly, preferably to an extent of at least 90% by weight, particularly preferably at least 95% by weight, of the compound of the formula (II).

In an alternative preferred embodiment of the process, the compound of the formula (I) is isolated from the product gas by absorption in an absorption medium and subsequent rectification of the loaded absorption medium. Here, the temperature of the product gas is reduced by direct and/or indirect cooling and the product gas is brought into contact in an absorption zone with an organic absorption medium which has a boiling point higher than that of the compound of the formula (I) under atmospheric pressure. Possible organic absorption media are, for example, those mentioned in DE-A 102009027401 and in DE-A 10336386. In addition to the compound of the formula (I), compound of the formula (II) is generally also absorbed by the absorption medium. The absorption zone is preferably located within an absorption column which is preferably equipped with separation-active internals. The compound of the formula (I) is isolated from the loaded absorption medium by rectification. In the rectification, the compound of the formula (I) is, as a result of appropriate selection of the number of theoretical plates, obtained in the form of a first fraction which consists predominantly, preferably to an extent of at least 90% by weight, particularly preferably at least 95% by weight, of the compound of the formula (I). The fractional condensation is particularly preferably configured, in particular in respect of the number of theoretical plates, so that, in addition to the compound of the formula (I) in the form of the first fraction, the unreacted compound of the formula (II) is obtained in the form of a second fraction which consists predominantly, preferably to an extent of at least 90% by weight, particularly preferably at least 95% by weight, of the compound of the formula (II).

The molar ratio of the compound of the formula (II) to formaldehyde is, in a preferred embodiment of the process of the invention, greater than 1 and can be up to 10. The molar ratio of the compound of the formula (II) to formaldehyde in the reaction gas is preferably from 1.1 to 5 and particularly preferably from 1.5 to 3.5.

The greater the molar ratio of the compound of the formula (II) to formaldehyde, the greater the amount of the compound of the formula (II) which is not reacted on contact with the catalyst and consequently is comprised in the product gas. The loss of unreacted compound of the formula (II) occurring via the product gas can thus be considerable when only the compound of the formula (I) prepared according to the invention is isolated from the product gas and utilized. To keep the loss of the compound of the formula (II) as small as possible, at least part of the compound of the formula (II) comprised in the product gas is recycled in a preferred embodiment of the process. For the purposes of the present invention, recycling refers to at least part of the compound of the formula (II) comprised in the product gas being used as at least part of the compound of the formula (II) comprised in the reaction gas. The compound of the formula (II) is preferably recycled in the form of the second fraction from the fractional condensation or from the rectification, which fraction consists, as described above, predominantly of the compound of the formula (II).

In an embodiment, the process of the invention comprises the preparation of acetic acid by partial oxidation of ethanol, wherein a gas mixture comprising ethanol and molecular oxygen is brought into contact with at least one solid oxidation catalyst whose active composition preferably comprises a vanadium oxide to form a product gas mixture. Here, ethanol is oxidized by means of molecular oxygen in a heterogeneously catalyzed manner to form acetic acid and water vapor. The conditions, in particular temperature and pressure, are set so that ethanol, acetic acid and water are present in gaseous or very predominantly gaseous form. The product gas mixture can be used directly as part of the reaction gas according to the invention.

In an alternative embodiment, the process of the invention comprises the preparation of acetic acid by homogeneously catalyzed carbonylation of methanol, wherein methanol and carbon monoxide are reacted in the liquid phase at a pressure of at least 30 bar (absolute). The reaction is carried out in the presence of a catalyst which comprises at least one of the elements Fe, Co, Ni, Ru, Rh, Pd, Cu, Os, Ir and Pt, an ionic halide and/or a covalent halide and also optionally a ligand such as $PR^3$ or $NR^3$, where $R^3$ is an organic radical.

EXAMPLES

Determination of Vanadium Oxidation States

The determination of the oxidation states of the catalysts was carried out by titrimetric volumetric analysis with potentiometric end point display (potentiograph with combined platinum electrode) under an inert gas atmosphere.

100-200 mg of the catalyst to be examined were dissolved in a mixture of 30 ml of aqueous $H_2SO_4$ and 10 ml of concentrated $H_3PO_4$ at the boiling point under inert gas. As aqueous $H_2SO_4$, use was made of a mixture of equal volumes of water and concentrated $H_2SO_4$.

For the analytical determination of the $V^{5+}$ content, the freshly prepared solution of the catalyst was titrated with a 0.1 molar aqueous ammonium iron sulfate standard solution $((NH_4)_2Fe(SO_4)_2)$. For the analytical determination of $V^{3+}$ and $V^{4+}$, a solution which had been freshly prepared in the corresponding way was titrated with a freshly prepared 0.02 molar aqueous potassium permanganate standard solution ($KMnO_4$), with one potential step ($V^{4+}$ to $V^{5+}$) occurring when only $V^{4+}$ to $V^{5+}$ were present and two potential steps ($V^{3+}$ to $V^{4+}$ and $V^{4+}$ to $V^{5+}$) occurring when $V^{3+}$ was present in addition to $V^{4+}$ to $V^{5+}$. After the quantitative oxidation of vanadium to $V^{5+}$, the solution was reduced to $V^{4+}$ using 0.1 N $(NH_4)_2Fe(SO_4)_2$ (control titration).

The number of moles $n(V^{3+})$, $n(V^{4+})$ and $n(V^{5+})$ was calculated from the respective amounts of the standard solution added.

The oxidation state is the mole fraction-weighted oxidation state of the various vanadium ions.

Experimental Plant:

An experimental plant equipped with a feed metering unit and an electrically heated, vertical reactor tube was used. The reactor used (stainless steel material No. 1.4541) had a tube length of 950 mm, an external diameter of 20 mm and an internal diameter of 16 mm. Four copper half-shells (E-Cu F25, external diameter 80 mm, internal diameter 16 mm, length 450 mm) were arranged around the reactor. The half shells were wound with a heating tape which in turn was wound with insulating tape. The temperature measurement for the reactor heating devices was carried out externally on the heating shell of the reactor. In addition, the temperature in the interior of the reactor could be determined over the entire catalyst bed by means of a thermocouple located in a central sheath (external diameter 3.17 mm, internal diameter 2.17 mm). At the lower end of the reactor tube, a wire mesh of a catalyst support device prevented discharge of the catalyst bed. The catalyst support device consisted of a 5 cm long tube (external diameter 14 cm, internal diameter 10 cm) over whose upper opening the wire mesh (1.5 mm mesh opening) was present. In the reactor tube, 14 g of an after-bed of steatite balls having a diameter of 3-4 mm (bed height 5 cm) were installed on this catalyst support device. The thermocouple sheath was placed centrally on the after-bed. 105 g of catalyst in the form of crushed material having a particle size of from 2.0 to 3.0 mm were then in each case introduced in undiluted form around the thermocouple sheath in the reaction tube (bed height 66 cm). Above the catalyst bed, there were 14 g of a preliminary bed of steatite balls having a diameter of 3-4 mm (bed height 5 cm).

Operation of the Experimental Plant:

A solution of trioxane in acetic acid was placed in a reservoir with a nitrogen breathing facility. The desired volume flow was metered by means of a Desaga KP 2000 pump and conveyed into a vaporizer coil. The solution was vaporized at 85° C. in the presence of preheated nitrogen. After vaporization was complete, the oxygen content was set to 2% by volume in some of the examples by introducing air. The gas mixture was heated to 180° C. in a preheater and introduced into the reactor. All gas flows were monitored by means of mass flow meters. Analytical ports at the reactor inlet and reactor outlet allowed analysis of the gas composition by on-line GC measurement. The pressure at the reactor inlet was set to a gauge pressure of ~0.15 bar by means of a manual pressure regulating valve downstream of the reactor.

The conversion of formaldehyde, $X_{Fd}$, was determined according to equation (1):

$$X_{Fd} = \frac{([Fd]_{in} + 3[Tri]_{in}) - \Delta V([Fd]_{out} + 3[Tri]_{out})}{[Fd]_{in} + 3[Tri]_{in}} 100\% \qquad (1)$$

where [X] is the concentration of component X (Fd=formaldehyde, Tri=trioxane) and the reactor inlet ($[X]_{in}$) and outlet ($[X]_{out}$) and $\Delta V$ is the volume change factor of the reaction, determined via the concentration change of the inert component nitrogen, where:

$$\Delta V = \frac{[N_2]_{in}}{[N_2]_{out}}$$

The selectivity ($S_{AA}$) of the conversion of formaldehyde into acrylic acid (Aa) was determined according to equation (2):

$$S_{AA} = \frac{\Delta V[As]_{out} - [Aa]_{in}}{[Fd]_{in} + 3[Tri]_{in}} 100\% \frac{1}{X_{Fd}} 100\% \qquad (2)$$

The reaction temperature (the temperature at the four copper half-shells) was 310° C. for each of the catalysts 1, 2, 4 and 5, and 325° C. for catalyst 3.

Production of Catalysts

Catalyst Precursor a (Production Scale):

4602 kg of isobutanol were placed in an 8 m³ steel/enamel stirred vessel which had been made inert by means of nitrogen and could be externally heated by means of pressurized water. After starting up the three-stage impeller stirrer, the isobutanol was heated to 90° C. under reflux. At this temperature, the addition of 690 kg of vanadium pentoxide by means of a transport screw was commenced. After about 20 minutes, after which about ⅔ of the desired amount of the vanadium pentoxide had been added, the pumping-in of 805 kg of 105% strength phosphoric acid was commenced while continuing to add vanadium pentoxide. After addition of the phosphoric acid, the reaction mixture was heated to about 100-108° C. under reflux and maintained under these conditions for 14 hours. The reaction mixture was subsequently drained into a heated pressure filter which had previously been made inert by means of nitrogen and was filtered at a temperature of about 100° C. and a pressure above the pressure filter of up to 3.5 bar. The filtercake was blown dry for about 1 hour by continual introduction of nitrogen at 100° C. while stirring by means of a centrally arranged stirrer having an adjustable height. The filter was subsequently heated to about 155° C. and evacuated to a pressure of 150 mbar ABS. Drying was continued to an isobutanol content of <2% by weight in the dried catalyst precursor.

The dried powder obtained was heated for 2 hours in air in a rotary tube having a length of 6.5 m, an internal diameter of 0.9 m and internal helical coils. The speed of rotation of the rotary tube was 0.4 rpm. The powder was fed at a rate of 60 kg/h into the rotary tube. Air was supplied at a rate of 100 m³/h. The temperatures measured directly on the outside of the tube reactor at five heating zones of equal length were 250° C., 300° C., 340° C., 340° C. and 340° C. After cooling to room temperature, the catalyst precursor was intimately mixed with 1% by weight of graphite and compacted in a roller compactor. The fines in the compacted material (particle size <400 µm) were sieved out and reintroduced into the compaction operation. The coarse material having a particle size of >400 µm was intimately mixed with a further 2% by weight of graphite. The catalyst precursor powder obtained in this way was pressed in a tableting machine to give 5.5×3.2×3 mm hollow cylinders (external diameter×height× diameter of the central hole). The pressing forces were about 10 kN.

Catalyst 1:

About 2.7 metric tons of the catalyst precursor a were fed continuously in a bed height of from 9 to 10 cm onto the gas-permeable conveyor belt of a belt calcination apparatus made up of two identical belt calcination apparatuses connected in series and having a total of eight calcination zones. The first 1.4 metric tons were used for establishment of operating parameters of the belt calcination apparatus. Since they do not represent uniform material, they were not taken into further consideration in the following. The belt calcination apparatus was operated at atmospheric pressure. An encapsulated transition zone was located between the calcination zones 4 and 5. To produce a gas circulation, each calcination zone comprised a fan. Each of the eight calcination zones was supplied with the desired amount of the desired fresh gas, with a corresponding amount of gas in each case being discharged in order to maintain the pressure of the atmosphere. The volume per unit time of gas circulating in each calcination zone was greater than the volume of the gas introduced or discharged per unit time. Between each two successive calcination zones, there was a dividing wall which reduced gas exchange and was open in the region of the stream of the catalyst precursor. The length of each calcination zone was 1.45 m. The speed of the conveyor belt was set to a value corresponding to the desired residence time of about 2 h per calcination zone. The individual zones were operated as shown in the following table:

| Zone | Temperature | Fresh gas introduced |
| --- | --- | --- |
| Calcination zone 1 | 140° C. | Air |
| Calcination zone 2 | 140° C. | Air |
| Calcination zone 3 | 260° C. | Air |
| Calcination zone 4 | 300° C. | Air |
| Transition zone | Cooling to 200° C. | Air |
| Calcination zone 5 | 335° C. | $N_2$ |
| Calcination zone 6 | 400° C. | $N_2/H_2O$ vapor (1:1) |
| Calcination zone 7 | 425° C. | $N_2/H_2O$ vapor (1:1) |
| Calcination zone 8 | 355° C. | $N_2$ |

Catalyst 2:

The catalyst precursor a was introduced into a convection oven (from Elino). 4500 standard l/h (standard liters per hour) of air were passed over the precursor while the temperature was increased from room temperature to 140° C. (heating rate 2.5° C./min). This temperature was maintained for a period of 168 minutes. The temperature was then increased to 260° C. (heating rate 5° C./min). This temperature was maintained for a period of 84 minutes. 2500 standard l/h of an $N_2$/air mixture (1:1) were then passed over the precursor while the temperature was increased to 325° C. (heating rate 3.2° C./min). This temperature was maintained for a period of 87 minutes. The temperature was then increased to 335° C. (heating rate 0.1° C./min). 4500 standard l/h of $N_2$ were then passed over the precursor while the temperature was maintained at 335° C. for 196 minutes. 1900 standard l/h of an $N_2/H_2O$ mixture (1:1) were passed over the precursor while the temperature was increased to 400° C. (heating rate 3.0° C./min). This temperature was maintained for a period of 86 minutes and subsequently increased at a heating rate of 3.125° C./min to 425° C. This temperature was maintained for 100 minutes. 4500 standard l/h of $N_2$ were then passed over the catalyst and the latter was cooled at an oven temperature of 355° C. (cooling rate 5° C./min). This temperature was maintained for 94 minutes. The oven was subsequently cooled to room temperature.

The hollow cylinders were comminuted in a compactor (Powtec RCC 100×20). For this purpose, the rollers on the compactor were removed and a 4 mm sieve was installed. Rotor shear head and screw rotated at 50 and 30 revolutions per minute, respectively. The 2-3 mm fraction was subsequently isolated by sieving.

Catalyst 3:

The catalyst precursor a was introduced into a convection oven (from Elino). 4500 standard l/h (standard liters per hour) of air were passed over the precursor while the temperature was increased from room temperature to 140° C. (heating rate 2.5° C./min). This temperature was maintained for a period of 168 minutes. The temperature was then increased to 380° C. (heating rate 2.5° C./min). 1900 standard l/h of an $N_2/H_2O$ mixture (1:1) were then passed over the precursor while the temperature was increased to 425° C. (heating rate 3.125° C./min). This temperature was maintained for a period of 206 minutes. The oven was finally cooled to room temperature. The hollow cylinders were then crushed manually in a porcelain mortar and the 2-3 mm fraction was isolated by sieving.

Catalyst 4:

212 g of catalyst 1 were placed in a porcelain dish and introduced in air into a muffle furnace (from Nabertherm). The catalyst was introduced in such a way that the hollow cylinders were not stacked. The catalyst was heated to 550° C. (heating rate 5° C./min) in a static air atmosphere. This temperature was maintained for 96 hours. The furnace was subsequently cooled to room temperature.

The catalyst rings were then crushed manually in a porcelain mortar and the 2-3 mm fraction was isolated by sieving.

Catalyst 5:

Catalyst 1 was introduced into a convection furnace (from Elino). 4500 standard l/h of air were passed over the precursor while the temperature was increased from room temperature to 550° C. (heating rate 2.5° C./min). This temperature was maintained for a period of 96 hours. The furnace was subsequently cooled to room temperature. The hollow cylinders were then crushed manually in a porcelain mortar and the 2-3 mm fraction was isolated by sieving.

Catalyst 6 (Reworking of Example 2 in U.S. Pat. No. 4,132,670):

An apparatus consisting of a 2.5 l glass precipitation vessel with impeller stirrer, a baffle, a thermostat from Haake (model B5), intensive reflux condenser, water separator and twin-chamber breather was used to precipitate the vanadium component.

200.98 g (1.1050 mol) of vanadium pentoxide (from GfE, batch: 80805) were slurried in a mixture consisting of 780 ml of isobutanol and 520 ml of benzyl alcohol. After refluxing for 5 hours, the resulting suspension comprised a black solid. The suspension was cooled to 60° C.

262.52 g (2.6520 mol) of 99% phosphoric acid (Sigma-Aldrich 04105-500G) were dissolved in 260 ml of isobutanol and the solution was slowly added dropwise over a period of 19 minutes. The mixture obtained was stirred under reflux for 20 hours. The resulting suspension comprised a light-blue solid. After cooling to room temperature, the solids were separated off by vacuum filtration. The filtercake was analyzed: it had a C content of 31.4 g/100 g, corresponding to a residual solvent content of 20% by weight. The solid was extruded to form catalyst pellets having a diameter of ⅛ inch. These pellets were dried at 150° C. for 2 hours.

Activation of the Catalyst Pellets (Method 1):

A vertically arranged fixed-bed reactor having an internal diameter of about 20 mm was charged with the catalyst pellets and the pellets were calcined in a first step for 6 hours at 300° C. in air (GHSV of about 2.0 vol/vol/min). The second calcination step was likewise carried out in air at a temperature of 450° C. for 12 hours. (GHSV of about 1.0 vol/vol/min)

The calcined pellets had a vanadium oxidation state of 4.23.

Activation of the Catalyst Pellets (Method 2):

A vertically arranged fixed-bed reactor having an internal diameter of about 20 mm was charged with the catalyst pellets and the pellets were calcined in a first step for 2 hours at 380° C. in air (GHSV of about 2.0 vol/vol/min). The second calcination step was likewise carried out in air at a temperature of 450° C. for 12 hours. (GHSV of about 1.0 vol/vol/min)

The calcined pellets had a vanadium oxidation state of 4.21.

The catalysts 1-5 were tested in the presence of a reaction gas comprising 2% by volume of $O_2$ (examples 1-5) in the experimental plant. BET surface area and oxidation state of the vanadium in the catalyst introduced in each case and also conversion of formaldehyde and selectivity of the conversion into acrylic acid at the beginning (0 h) and after a time on stream of 30 h are shown in the following table.

|  | Cat. 1 | Cat. 2 | Cat. 3 | Cat. 4 | Cat. 5 |
| --- | --- | --- | --- | --- | --- |
| $V_{Ox}$ | 4.14 | 4.27 | 4.48 | 4.86 | 4.93 |
| BET | 31 m²/g | 19 m²/g | 13 m²/g | 18 m²/g | 20 m²/g |
| Temp. | 310° C. | 310° C. | 325° C. | 310° C. | 310° C. |
|  | Example 1* | Example 2* | Example 3 | Example 4 | Example 5 |
| $[O2]_{in}$ | 2.0% by volume | 2.0% by volume | 2.0% by volume | 2.0% by volume | 2.0% by volume |
| $[Fd]_{in}$ | 0.0% by volume | 0.2% by volume | 0.1% by volume | 0.1% by volume | 0.1% by volume |
| $[Tri]_{in}$ | 1.4% by volume | 1.3% by volume | 1.2% by volume | 1.3% by volume | 1.4% by volume |
| $[Ac]_{in}$ | 9.4% by volume | 9.5% by volume | 9.1% by volume | 9.4% by volume | 9.5% by volume |
| GVS | 43 standard l/h | 43 standard l/h | 43 standard l/h | 43 standard l/h | 43 standard l/h |
| $X_{Fd}(t=0\ h)$ | 75% | 66% | 75% | 80% | 86% |
| $S_{Aa}(t=0\ h)$ | 79% | 71% | 83% | 90% | 80% |
| $X_{Fd}(t=30\ h)$ | 71% | 62% | 68% | 77% | 83% |
| $S_{Aa}(t=30\ h)$ | 54% | 50% | 67% | 83% | 74% |

*Comparative example

All values given for specific surface areas of the catalysts relate to determinations in accordance with DIN 66131 (Determinations of the specific surface area of solids by gas adsorption ($N_2$) by the Brunauer-Emmet-Teller (BET) method).

Example 5 was repeated without air being introduced into the reaction gas (example 6). The following results were obtained:

|  | Example 6* |
| --- | --- |
| $[O2]_{in}$ | 0% by volume |
| $[Fd]_{in}$ | 0.1% by volume |
| $[Tri]_{in}$ | 1.4% by volume |

-continued

| | Example 6* |
|---|---|
| $[Ac]_{in}$ | 9.5% by volume |
| GVS | 43 standard l/h |
| $X_{Fd}(t = 0\ h)$ | 83% |
| $S_{Aa}(t = 0\ h)$ | 82% |
| $X_{Fd}(t = 30\ h)$ | 46% |
| $S_{Aa}(t = 30\ h)$ | 76% |

*Comparative example

The invention claimed is:

1. A process for preparing a compound of formula (I),

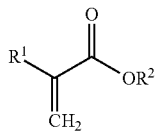

(I)

where $R^1$ and $R^2$ are each, independently of one another, H or $(C_1\text{-}C_4)$-alkyl, the process comprising contacting (i) a reaction gas comprising gaseous formaldehyde, molecular oxygen and a gaseous compound of formula (II)

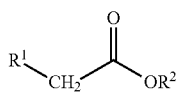

(II)

with (ii) a solid catalyst whose active composition comprises a vanadium-phosphorus oxide having an average oxidation state of vanadium of from greater than +4.65 to +5.0, to obtain a product gas comprising the compound of the formula (I).

2. The process according to claim 1, wherein the reaction gas further comprises an inert diluent gas.

3. The process according to claim 1, wherein the active composition comprises a vanadium-phosphorus oxide having an average oxidation state of vanadium of from greater than +4.69 to +5.0.

4. The process according to claim 1, wherein the vanadium-phosphorus oxide has a phosphorus-vanadium atomic ratio of from 0.9 to 2.0.

5. The process according to claim 1, wherein $R^1$ and $R^2$ in the compounds of the formulae (I) and (II) are H or $CH_3$.

6. The process according to claim 1, wherein the compound of the formula (I) is acrylic acid and the compound of the formula (II) is acetic acid.

7. The process according to claim 1, wherein the reaction gas is brought into contact with the solid catalyst at a temperature from 250 to 400° C.

8. The process according to claim 1, wherein the reaction gas comprises from 0.1 to 10% by volume of molecular oxygen.

9. The process according to claim 1, wherein the reaction gas comprises from 0.5 to 10% by volume of formaldehyde.

10. The process according to claim 1, wherein the reaction gas comprises from 1.5 to 20% by volume of the compound of the formula (II).

11. The process according to claim 1, wherein the molar ratio of the compound of the formula (II) to formaldehyde is from 1 to 10.

12. The process according to claim 1, wherein the compound of the formula (I) is obtained by fractional condensation of the product gas.

13. The process according to claim 1, wherein the compound of the formula (I) is isolated from the product gas by absorption in an absorption medium and subsequent rectification of the loaded absorption medium.

14. The process according to claim 1, wherein an all-active shaped catalyst body consisting of active composition is obtained by reacting a pentavalent vanadium compound with an organic, reducing solvent in the presence of a pentavalent phosphorus compound to give a catalyst precursor composition, shaping the catalyst precursor composition to give the shaped catalyst precursor bodies and treating the latter in an atmosphere comprising molecular oxygen at from 250 to 700° C.

15. The process according to claim 1, further comprising preparing the formaldehyde (i) from a formaldehyde source selected from the group consisting of trioxane, paraformaldehyde, formalin, methylal, aqueous paraformaldehyde solution and aqueous formaldehyde solution, or (ii) by heterogeneously catalyzed partial gas-phase oxidation of methanol.

16. The process according to claim 6, further comprising preparing the acetic acid by partial oxidation of ethanol or by homogeneously catalyzed carbonylation of methanol.

* * * * *